United States Patent
Srinivasan et al.

(10) Patent No.: US 9,649,452 B2
(45) Date of Patent: May 16, 2017

(54) ACTIVE SAFETY PEN NEEDLE ASSEMBLY

(71) Applicant: Becton, Dickinson and Company, Franklin Lakes, NJ (US)

(72) Inventors: Sudarsan Srinivasan, Wayne, NJ (US); Amit Limaye, Wayne, NJ (US); Michael DiBiasi, West Milford, NJ (US); Sean Sullivan, Ridgewood, NJ (US); David Schiff, Highland Park, NJ (US); Todd Sack, Dover, DE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 99 days.

(21) Appl. No.: 14/564,634

(22) Filed: Dec. 9, 2014

(65) Prior Publication Data

US 2015/0157807 A1 Jun. 11, 2015

Related U.S. Application Data

(60) Provisional application No. 61/914,009, filed on Dec. 10, 2013.

(51) Int. Cl.
*A61M 5/32* (2006.01)
*A61M 5/50* (2006.01)

(52) U.S. Cl.
CPC .......... *A61M 5/3245* (2013.01); *A61M 5/321* (2013.01); *A61M 5/326* (2013.01);
(Continued)

(58) Field of Classification Search
CPC . A61M 5/3243; A61M 5/3257; A61M 5/3271
(Continued)

(56) References Cited

U.S. PATENT DOCUMENTS

| 4,894,055 A | 1/1990 | Sudnak |
| 4,897,083 A | 1/1990 | Martell |

(Continued)

FOREIGN PATENT DOCUMENTS

| DE | 8909799 U1 | 11/1989 |
| DE | 102006022081 B3 | 1/2008 |

(Continued)

OTHER PUBLICATIONS

Clickfine® AutoProtect™; YPSOMED Selfcare Solutions; www.ypsomed.com/b2b@ypsomed.com.

*Primary Examiner* — Deanna K Hall
(74) *Attorney, Agent, or Firm* — Dickinson Wright PLLC

(57) ABSTRACT

The subject invention provides a safety pen needle assembly which includes: a hub; a needle carrier; a needle fixed to the needle carrier; a shield; and, a first engageable locking arrangement for fixing the shield to the needle carrier. Upon a predetermined extent of distal movement of the shield relative to the hub, the first locking arrangement is engaged such that the shield becomes fixed to the needle carrier. Upon further distal movement of the shield relative to the hub beyond the predetermined extent of distal movement, the shield and the needle carrier move in concert together relative to the hub causing a proximal end of the needle to move distally relative to the hub to a retracted state. Advantageously, the subject invention provides a reliable, low-cost safety pen needle assembly which does not require a spring or other biasing element.

5 Claims, 12 Drawing Sheets

(52) U.S. Cl.
CPC ........ *A61M 5/3213* (2013.01); *A61M 5/3243* (2013.01); *A61M 5/3257* (2013.01); *A61M 5/3271* (2013.01); *A61M 5/50* (2013.01); *A61M 2005/3254* (2013.01)

(58) Field of Classification Search
USPC .................................................. 604/192, 198
See application file for complete search history.

(56) References Cited

U.S. PATENT DOCUMENTS

| | | | |
|---|---|---|---|
| 4,998,924 | A | 3/1991 | Ranford |
| 5,061,246 | A | 10/1991 | Anapliotis |
| 5,193,552 | A | 3/1993 | Columbus et al. |
| 5,246,428 | A | 9/1993 | Falknor |
| 5,250,037 | A | 10/1993 | Bitdinger |
| 5,256,153 | A | 10/1993 | Hake |
| 5,269,765 | A | 12/1993 | Kuracina |
| 5,279,579 | A | 1/1994 | D'Amico |
| 5,292,314 | A | 3/1994 | D'Alessio et al. |
| 5,336,197 | A | 8/1994 | Kuracina et al. |
| 5,364,362 | A | 11/1994 | Schulz |
| 5,389,085 | A | 2/1995 | D'Alessio et al. |
| 5,417,662 | A | 5/1995 | Hjertman et al. |
| 5,429,612 | A | 7/1995 | Berthier |
| 5,514,097 | A | 5/1996 | Knauer |
| 5,562,624 | A | 10/1996 | Righi et al. |
| 5,591,138 | A | 1/1997 | Vaillancourt |
| 5,609,577 | A | 3/1997 | Haber et al. |
| 5,634,906 | A | 6/1997 | Haber et al. |
| 5,688,241 | A | 11/1997 | Asbaghi |
| 5,795,336 | A | 8/1998 | Romano et al. |
| 5,810,775 | A | 9/1998 | Shaw |
| 5,873,856 | A | 2/1999 | Hjertman et al. |
| 5,971,966 | A | 10/1999 | Lav |
| RE36,398 | E | 11/1999 | Byrne et al. |
| 5,984,899 | A | 11/1999 | D'Alessio et al. |
| RE36,447 | E | 12/1999 | Byrne et al. |
| 6,017,329 | A | 1/2000 | Hake |
| 6,110,147 | A | 8/2000 | Perouse |
| 6,203,529 | B1 | 3/2001 | Gabriel et al. |
| 6,224,576 | B1 | 5/2001 | Thorne et al. |
| 6,379,336 | B1 | 4/2002 | Asbaghi et al. |
| 6,547,764 | B2 | 4/2003 | Larsen et al. |
| 6,569,124 | B1 | 5/2003 | Perouse |
| 6,692,463 | B1 | 2/2004 | Marteau et al. |
| 6,773,415 | B2 | 8/2004 | Heiniger |
| 6,796,967 | B2 | 9/2004 | Jensen |
| 6,855,129 | B2 | 2/2005 | Jensen et al. |
| 6,939,330 | B1 | 9/2005 | McConnell-Montalvo et al. |
| 6,986,760 | B2 | 1/2006 | Giambattista et al. |
| 7,066,907 | B2 | 6/2006 | Crossman et al. |
| 7,074,211 | B1 | 7/2006 | Heiniger et al. |
| 7,147,624 | B2 | 12/2006 | Hirsiger et al. |
| 7,198,617 | B2 | 4/2007 | Millerd |
| 7,229,432 | B2 | 6/2007 | Marshall et al. |
| 7,278,986 | B1 | 10/2007 | Frost |
| 7,361,160 | B2 | 4/2008 | Hommann et al. |
| 7,361,166 | B2 | 4/2008 | Bosse et al. |
| 7,370,759 | B2 | 5/2008 | Hommann |
| 7,374,558 | B2 | 5/2008 | Kirchhofer |
| 7,384,414 | B1 | 6/2008 | Marshall et al. |
| 7,442,185 | B2 | 10/2008 | Amark et al. |
| 7,540,858 | B2 | 6/2009 | DiBiasi |
| 7,635,350 | B2 | 12/2009 | Scherer |
| 8,177,745 | B2 | 5/2012 | Brechbuehler et al. |
| 2002/0193746 | A1 | 12/2002 | Chevallier |
| 2003/0014018 | A1 | 1/2003 | Giambattista et al. |
| 2003/0120209 | A1 | 6/2003 | Jensen et al. |
| 2004/0122379 | A1 | 6/2004 | Bosse et al. |
| 2005/0113750 | A1 | 5/2005 | Targell |
| 2005/0267140 | A1 | 12/2005 | Koska |
| 2005/0277893 | A1 | 12/2005 | Liversidge |
| 2005/0288607 | A1 | 12/2005 | Konrad |
| 2006/0095010 | A1 | 5/2006 | Westbye |
| 2006/0270984 | A1 | 11/2006 | Hommann |
| 2007/0027430 | A1 | 2/2007 | Hommann |
| 2007/0129674 | A1 | 6/2007 | Liversidge |
| 2007/0156101 | A1 | 7/2007 | Liversidge |
| 2007/0173772 | A1 | 7/2007 | Liversidge |
| 2007/0255225 | A1 | 11/2007 | Alchas et al. |
| 2008/0009807 | A1 | 1/2008 | Hommann |
| 2008/0071225 | A1 | 3/2008 | Hommann et al. |
| 2008/0077093 | A1 | 3/2008 | Gratwohl et al. |
| 2008/0103453 | A1 | 5/2008 | Liversidge |
| 2008/0103454 | A1 | 5/2008 | Gratwohl et al. |
| 2008/0177237 | A1 | 7/2008 | Stonehouse et al. |
| 2008/0249477 | A1 | 10/2008 | Paproski et al. |
| 2008/0255526 | A1 | 10/2008 | Bosse et al. |
| 2008/0262436 | A1 | 10/2008 | Olson |
| 2008/0269691 | A1 | 10/2008 | Cowe |
| 2009/0005742 | A1 | 1/2009 | Liversidge |
| 2009/0221972 | A1 | 9/2009 | Gratwohl et al. |
| 2009/0259178 | A1 | 10/2009 | Bechbuehler et al. |
| 2009/0259196 | A1 | 10/2009 | Gratwohl et al. |
| 2010/0114035 | A1 | 5/2010 | Schubert et al. |
| 2011/0178473 | A1* | 7/2011 | Richards ............. A61M 5/3257 604/198 |
| 2012/0150125 | A1 | 6/2012 | Karlsson et al. |

FOREIGN PATENT DOCUMENTS

| | | |
|---|---|---|
| DE | 102006041810 A1 | 3/2008 |
| EP | 1464353 A1 | 10/2004 |
| EP | 1747789 A2 | 1/2007 |
| FR | 2881053 A1 | 7/2006 |
| WO | 90/02515 A1 | 3/1990 |
| WO | 92/09319 A1 | 6/1992 |
| WO | 92/20281 A1 | 11/1992 |
| WO | 01/91837 A1 | 12/2001 |
| WO | 01/93924 A1 | 12/2001 |
| WO | 03/045480 A1 | 6/2003 |
| WO | 03/105935 A2 | 12/2003 |
| WO | 2004/000397 A1 | 12/2003 |
| WO | 2004030539 A1 | 4/2004 |
| WO | 2004/071560 A1 | 8/2004 |
| WO | 2005/097238 A2 | 10/2005 |
| WO | 2006018626 A1 | 2/2006 |
| WO | 2006/072807 A1 | 7/2006 |
| WO | 2007/077463 A1 | 7/2007 |
| WO | 2008/025179 A1 | 3/2008 |
| WO | 2008/028304 A1 | 3/2008 |
| WO | 2008/028305 A1 | 3/2008 |
| WO | 2008/028312 A1 | 3/2008 |
| WO | 2008/035122 A1 | 3/2008 |
| WO | 2008/043188 A1 | 4/2008 |
| WO | 2008/044067 A1 | 4/2008 |
| WO | 2008/050158 A2 | 5/2008 |
| WO | 2008/083037 A1 | 7/2008 |
| WO | 2009/003300 A1 | 1/2009 |
| WO | 2009/030056 A1 | 3/2009 |
| WO | 2009/114762 A1 | 9/2009 |
| WO | 2010/126432 A1 | 11/2010 |

\* cited by examiner

ACTIVE SAFETY PEN NEEDLE ASSEMBLY

CROSS-REFERENCE TO RELATED APPLICATION

This application claims priority to U.S. Provisional Patent Application No. 61/914,009, filed Dec. 10, 2013, the entire contents of which are incorporated by reference herein.

BACKGROUND OF THE INVENTION

Safety pen needle assemblies are known in the prior art for shielding a used needle post-injection. Such assemblies may be generally classified as "passive" or "active". A passive device is typically considered to be one where shielding may be achieved without requiring additional steps beyond that required to conduct an injection. In contrast, an active device is typically considered to be one where shielding requires one or more additional steps beyond that required to conduct an injection, such as, for example, triggering a spring-fired shield.

In addition, shielding is most commonly utilized with the distal, patient end of the needle. Shielding has been also provided for the proximal, non-patient end of the needle and has been provided on the same device for both the distal and proximal ends of the needle post-injection. U.S. Pat. No. 7,540,858 to DiBiasi and U.S. Published Patent Application No. 2011/0178473 A1 to Richards et al., both to the assignee herein, show passive dual end shielding safety pen needle assemblies where both the distal and proximal ends of the needle may be shielded passively post-injection.

SUMMARY OF THE INVENTION

The subject invention provides an active safety pen needle assembly which includes: a hub having features for mounting onto a medical injector; a needle carrier; a needle fixed to the needle carrier, the needle including proximal and distal ends, the distal end formed for insertion into a patient; a shield; and, a first engageable locking arrangement for fixing the shield to the needle carrier so that the shield and the needle carrier move in concert. In an initial state, the shield is moveable relative to the needle carrier. Upon a predetermined extent of distal movement of the shield relative to the hub, the first locking arrangement is engaged such that the shield becomes fixed to the needle carrier. Upon further distal movement of the shield relative to the hub beyond the predetermined extent of distal movement, the shield and the needle carrier move in concert together relative to the hub causing the proximal end of the needle to move distally relative to the hub to a retracted state. Advantageously, the subject invention provides a reliable, low-cost safety pen needle assembly which does not require a spring or other biasing element.

These and other features of the invention will be better understood through a study of the following detailed description and accompanying drawings.

DETAILED DESCRIPTION OF THE INVENTION

Figure 1:
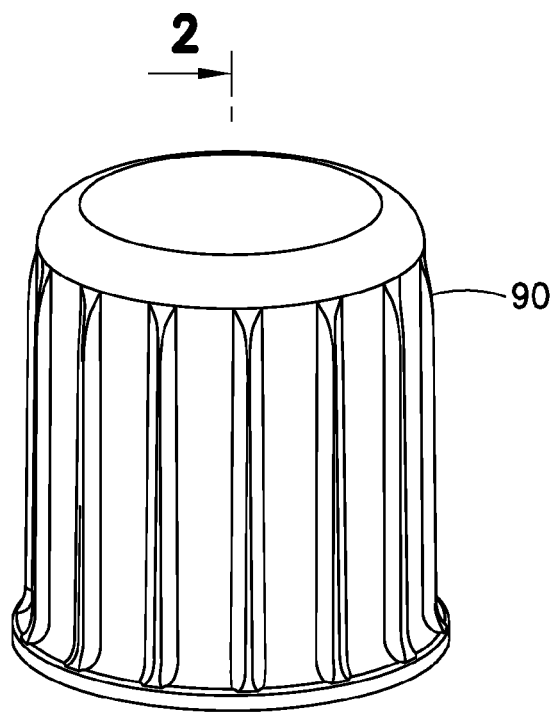
FIG. 1 is a perspective view of a safety pen needle assembly formed in accordance with the subject invention accommodated in an outer casing.

With reference to the Figures, a safety pen needle assembly 10 is shown which generally includes a hub 12, a needle carrier 14, a needle 16, and a shield 18. The safety pen needle assembly 10 may be used with various medical injectors, but is particularly well-suited for use with medical pen injectors.

As used herein, the term "distal", and derivatives thereof, refer to a direction generally towards a patient, while, the term "proximal", and derivatives thereof, refer to a direction generally away from a patient.

The hub 12 is generally tubular and includes feature 20, such as threads or a bayonet-lock feature, for mounting onto a medical injector. The feature 20 may be a surface formation or other mounting arrangement, such as a friction-fit (e.g., tapered (luer)) surface, snap-on features, and so forth. A stop 21 may be provided to define a final mounting position relative to an injector.

The needle carrier 14 is generally tubular and formed to telescopingly receive the hub 12. The needle 16 is fixed to the needle carrier 14 with a distal end 22, formed for insertion into a patient, located distally from the needle carrier 14, and a proximal end 24 located proximally from the needle carrier 14. The needle 16 may be of any known configuration capable of conveying fluid between the distal and proximal ends 22, 24, e.g., being a cannula having a hollow lumen therein extending through the needle 16.

The shield 18 includes a sidewall 26 formed to encircle the needle carrier 14. The sidewall 26 includes proximal and distal ends 28, 30. The proximal and distal ends 28, 30 surround proximal and distal openings 32, 34, respectively, each configured to permit passage therethrough of the needle 16. Optionally, a covering wall 36 may extend between the distal opening 34 and the sidewall 26. The covering wall 36 may act to impede access to the distal end 22 of the needle 16, particularly in a post-use state as discussed below. As will be appreciated by those skilled in the art, the covering wall 26 may not be necessary if, for example, the sidewall 26 is provided with sufficient length to impede such access.

A first locking arrangement 38 is provided for fixing the shield 18 to the needle carrier 14 so that the shield 18 and the needle carrier 14 may move together in concert. The first locking arrangement 38 may be of any configuration which is engageable with sufficient relative movement, e.g., axial movement, between the shield 18 and the needle carrier 14. By way of non-limiting example, the needle shield 18 may be provided with a detent 40, e.g., in the sidewall 26, for snap engagement with a recess 42 formed in the needle carrier 14. The shield 18 is formed with sufficient inherent memory to maintain snap engagement between the detent 40 and the recess 42. It is preferred that the detent 40 be provided on a cantilevered arm 44. Alternatively, the constituent material of the sidewall 26 may be utilized to provide the inherent memory. As will be appreciated by those skilled in the art, a plurality of the first locking arrangements 38 may be provided (e.g., a plurality of sets of detents 40/recesses 42).

A ramped surface 46 is preferably provided adjacent to the recess 42 to allow the detent 40 to by-pass in one direction, over the ramped surface 46 in a rising direction. The ramped surface 46 defines a step 48 adjacent the recess 42 to inhibit movement of the detent 40 in the reverse direction. In addition, a channel 50 may be provided in the needle carrier 14 formed to accommodate sliding movement of the detent 40. Preferably, the channel 50 is generally parallel to a longitudinal axis of the needle carrier 14 and longitudinally aligned with the recess 42.

Figure 2:
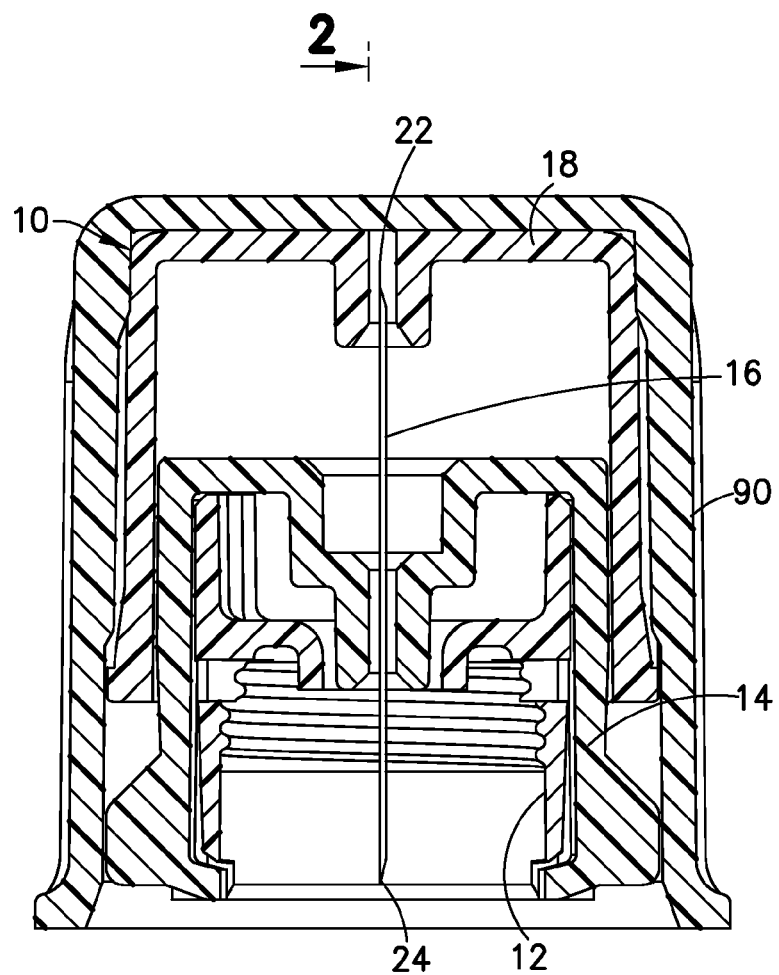
FIG. 2 is a cross-sectional view taken along line 2-2 of FIG. 1.
Figure 3:
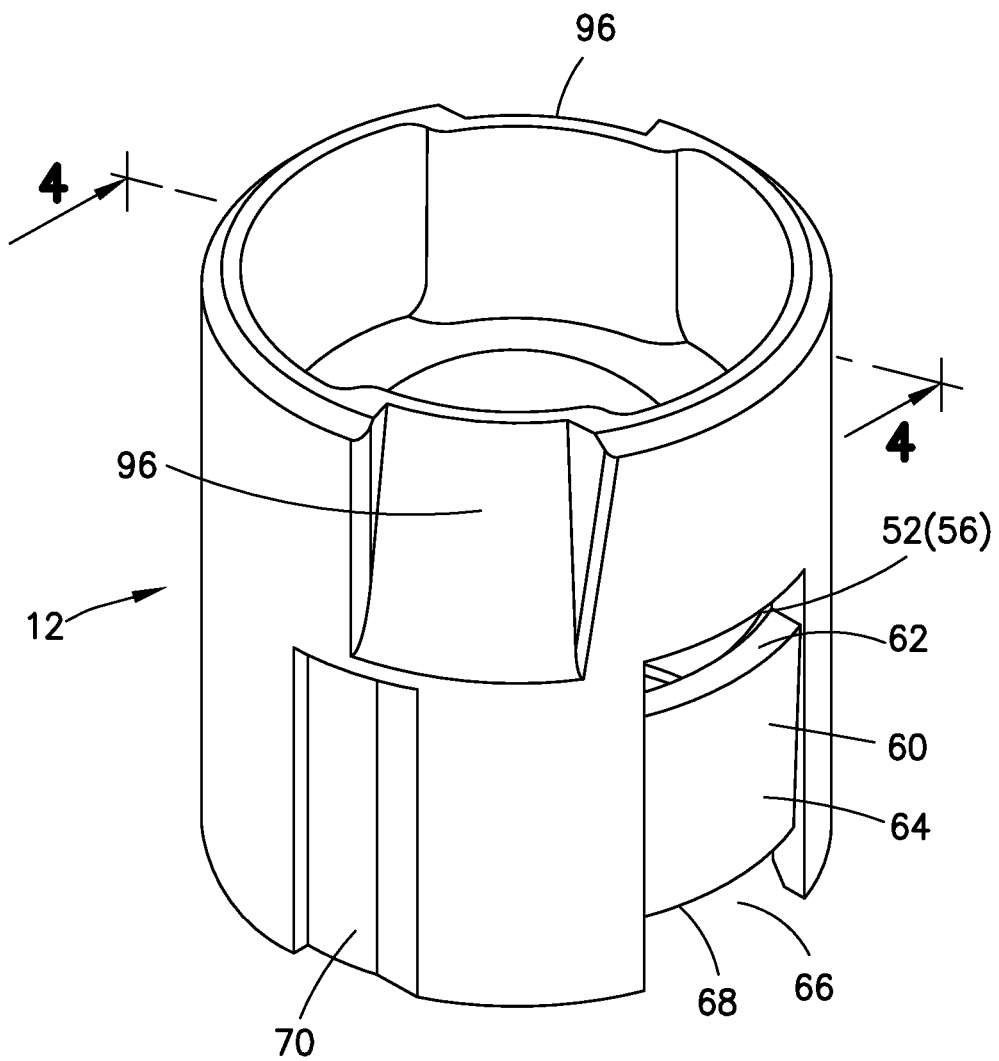
FIGS. 3-5 are various views of a hub useable with the subject invention.
Figure 4:
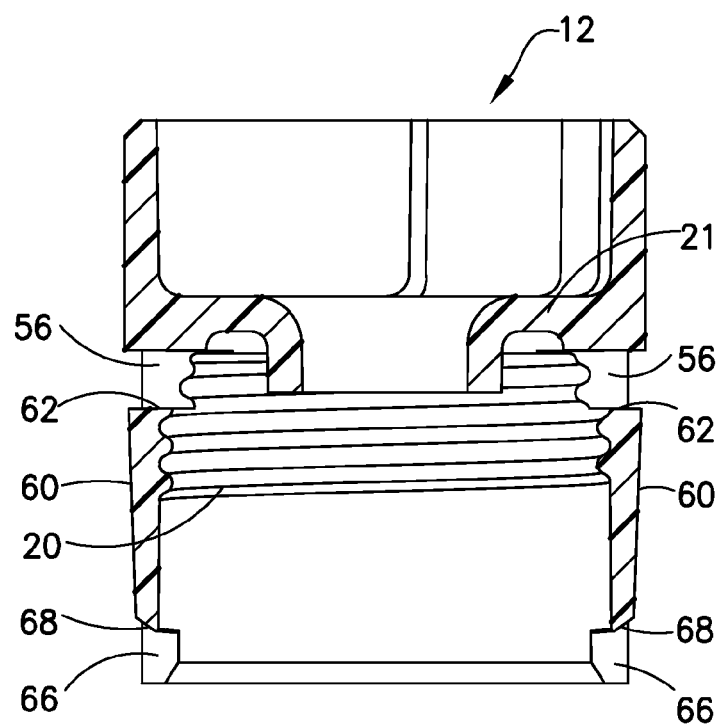
Figure 5:
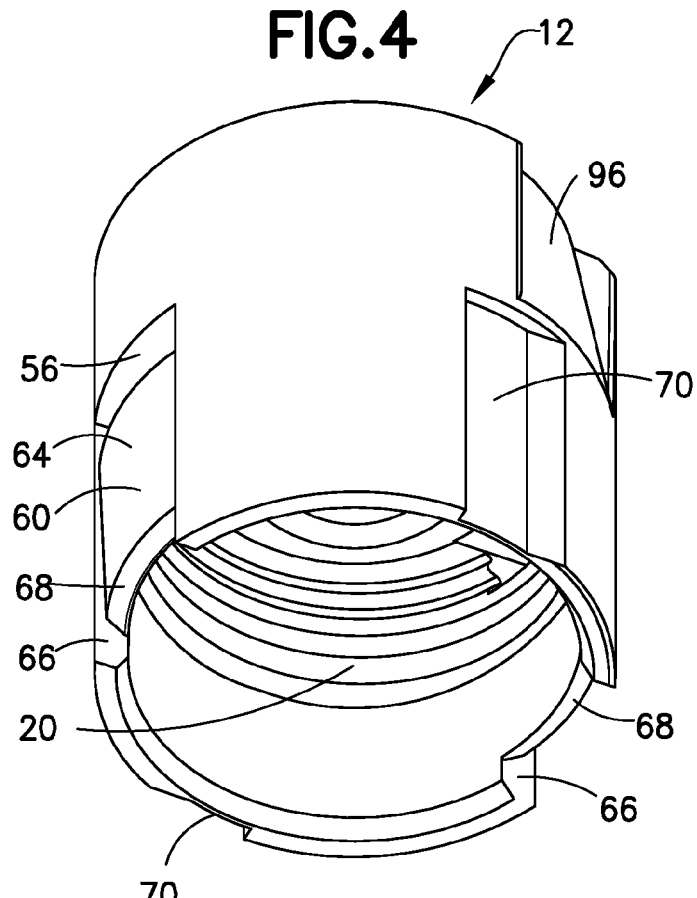
Figure 6:
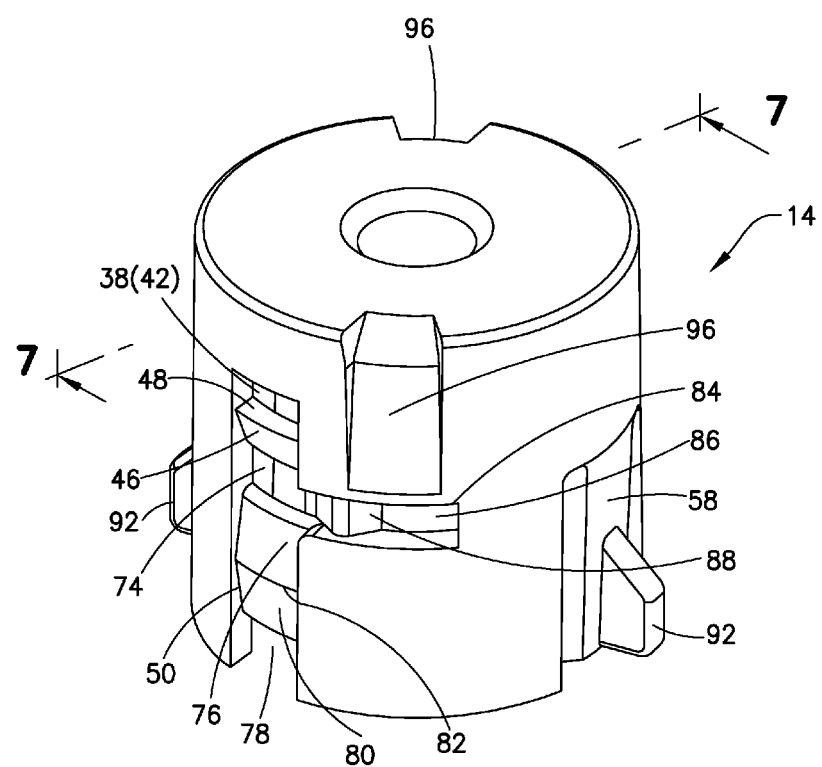
FIGS. 6-8 are various views of a needle carrier useable with the subject invention.
Figure 7:
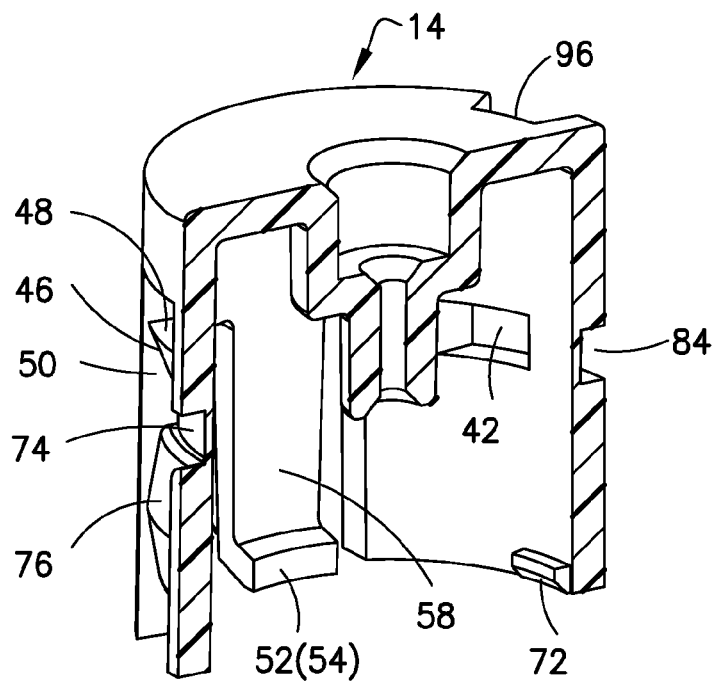
Figure 13:
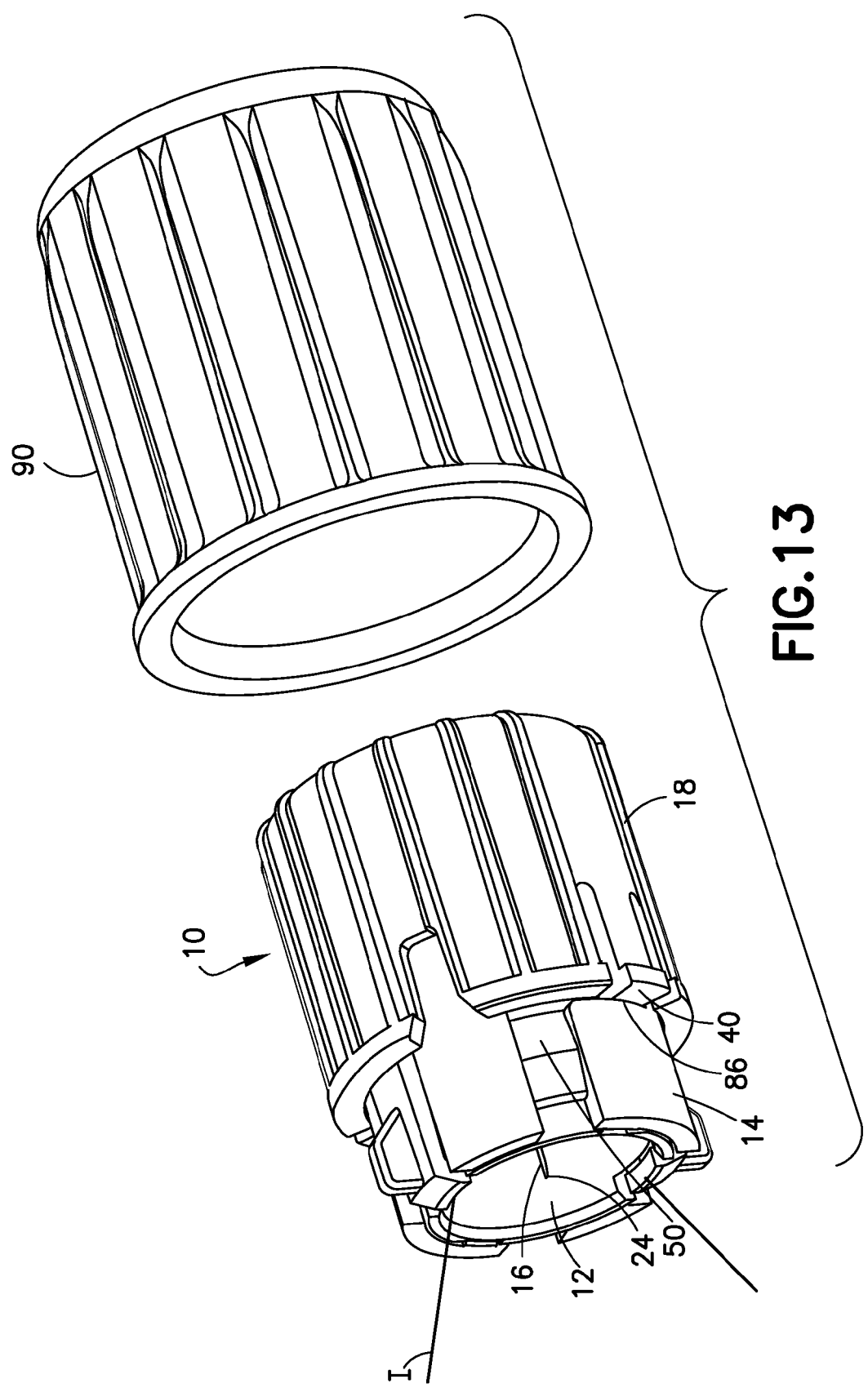

With reference to FIG. 13, for use, the safety pen needle assembly 10 is mounted onto a medical injector I, in particular with the feature 20 of the hub 12 cooperatively engaging a corresponding feature (e.g., threads) on the injector I. Once mounted, the injector I may be prepared for injection, for example by priming the needle 16. As shown in FIG. 2, in an initial state, the shield 18 may be located to cover the distal end 22 of the needle 16. Alternatively, the distal end 22 may be initially exposed so as to provide visual access to a user for priming and insertion into a patient. Once prepared, the needle 16 may be inserted into a patient. Depending on the initial position of the shield 18 relative to the hub 12, the shield 18 may be forced proximally due to contact with the patient's skin. Interengagement of the shield 18 with portion(s) of the needle carrier 14 and/or interengagement of the shield 18 with the patient's skin shall limit proximal movement of the shield 18. With the needle 16 being exposed, an injection may be administered.

Figure 15:
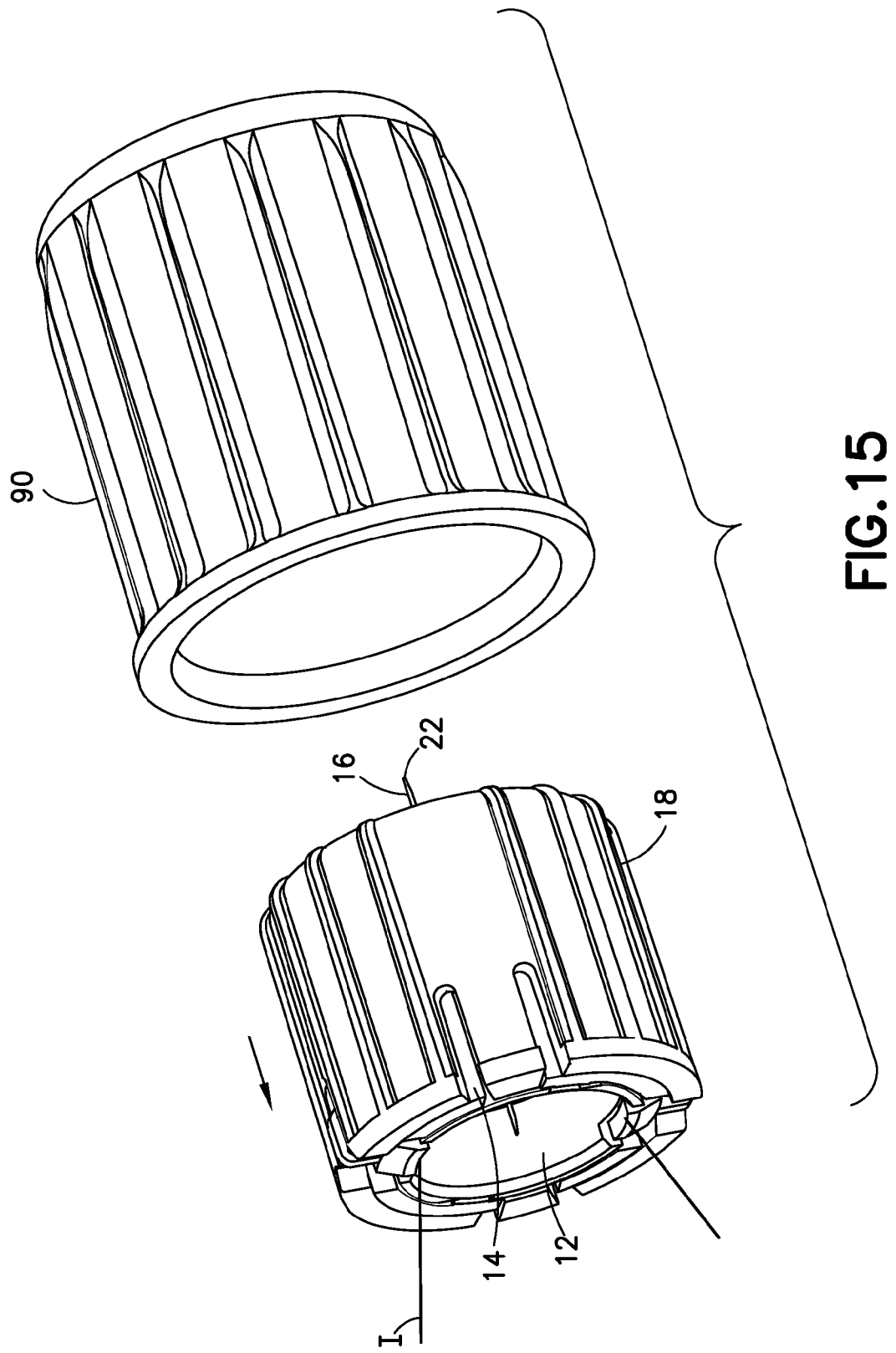
Figure 16:
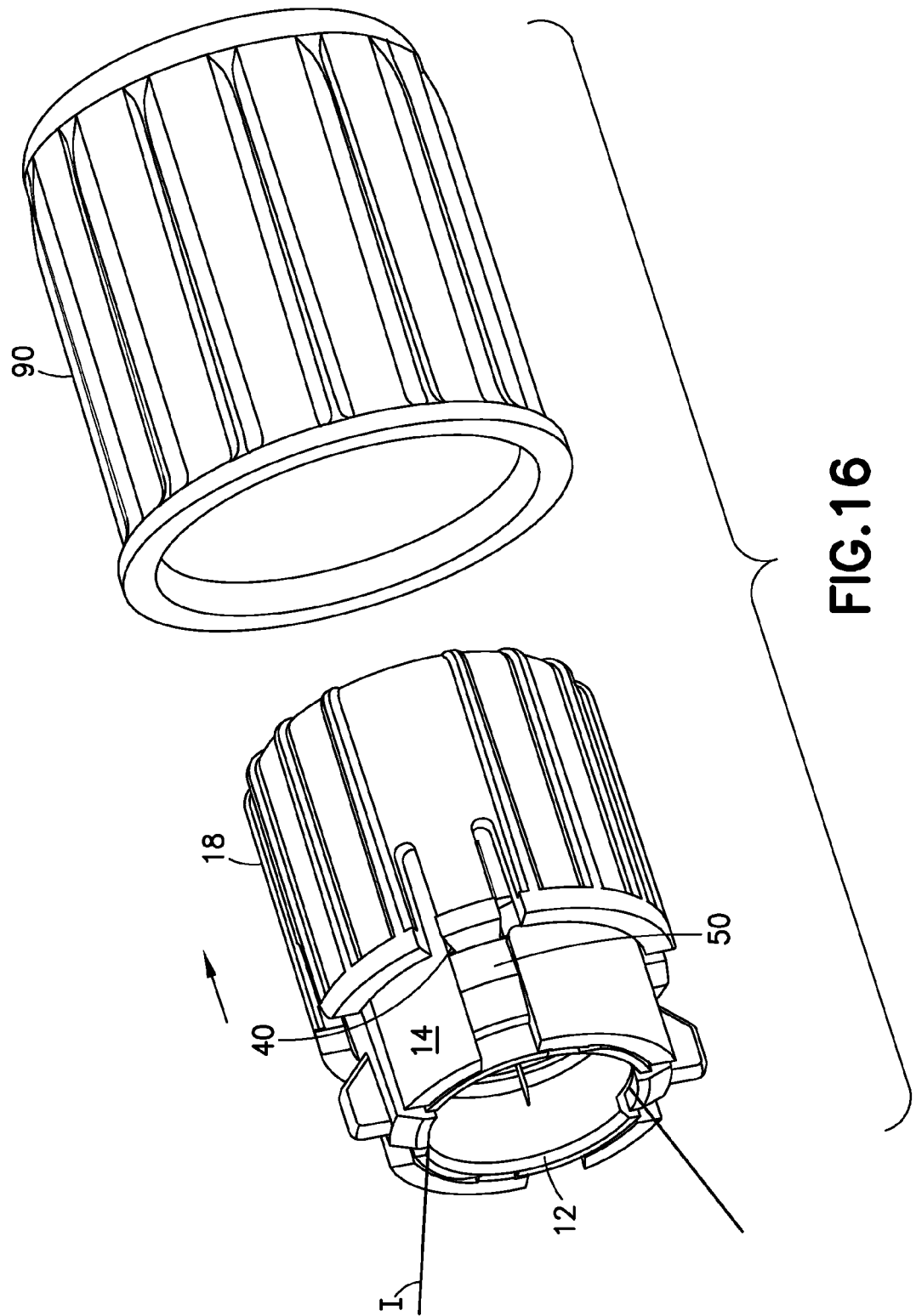
Figure 17:
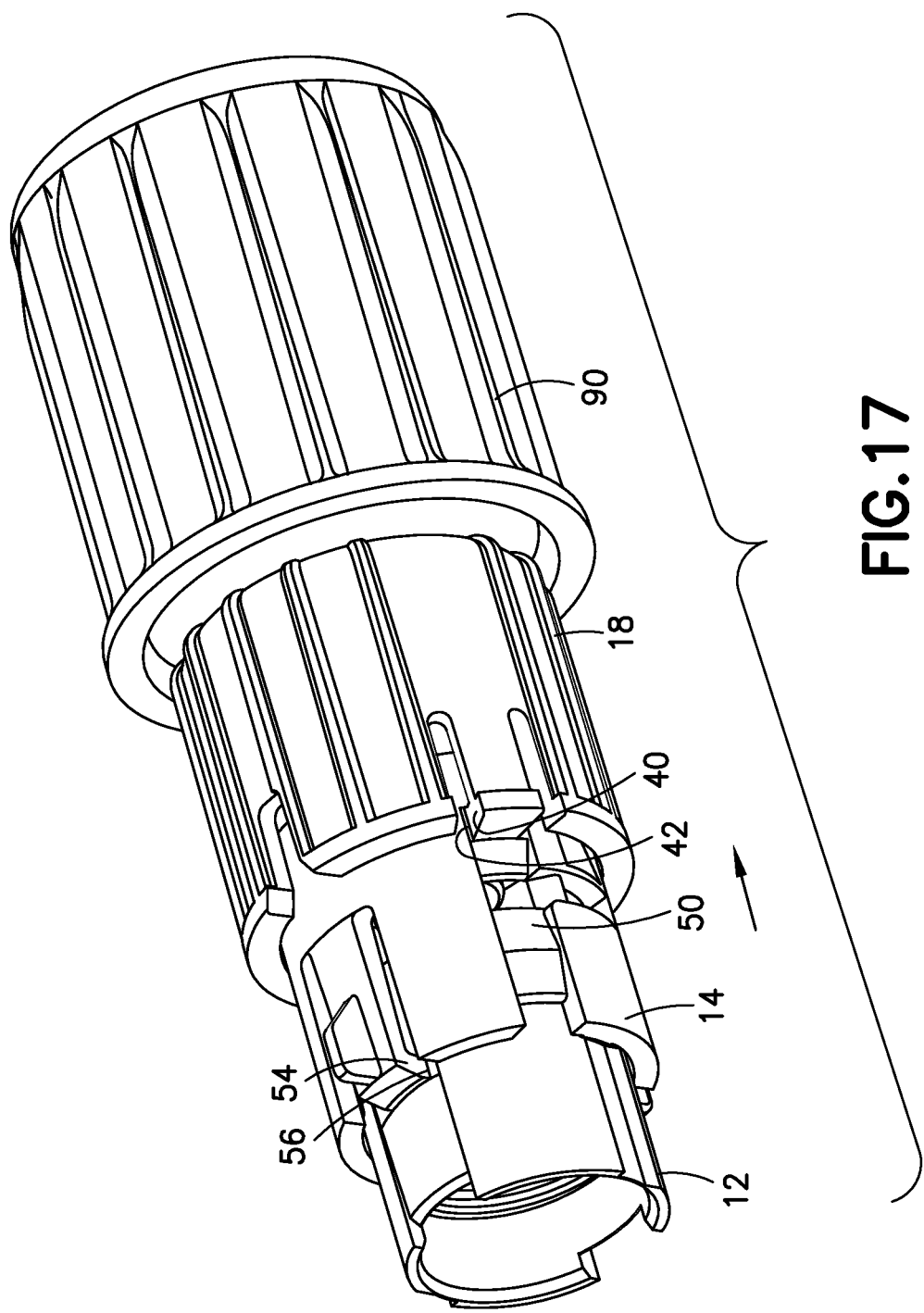

Once the injection is completed, the needle 16 is removed from the patient, as shown in FIG. 15, with the distal end 22 of the needle 16 being exposed. As shown in FIG. 16, with the safety pen needle assembly 10 being maintained on the injector I, the shield 18 is urged distally relative to the hub 12 until the first locking arrangement 38 is engaged. Here, as shown in FIG. 17, the detent 40 may be seated in the recess 42. Further distal advancement of the shield 18 relative to the hub 12 causes the shield 18 and the needle carrier 14 to move in concert. As shown between FIGS. 16 and 17, with the needle carrier 14 moving distally relative to the hub 12, the proximal end 24 of the needle 16 is caused to be retracted relative to the hub 12. The proximal end 24 of the needle 16 is retracted sufficiently relative to the hub 12 so as to restrict inadvertent access thereto by a user post-injection. For example, the proximal end 24 of the needle 16 may be retracted to be located 0.25", or more, within the hub 12. Thereafter, the safety pen needle assembly 10 may be removed from the injector I and disposed.

With the subject invention, the distal advancement of the shield 18 is provided manually by a user with the hub 12 being maintained on the injector I after injection. Continuous distal displacement of the shield 18, with the hub 12 maintained on the injector I, results in sequential distal displacement of the shield 18 and the needle carrier 14. This provides for active activation of shielding. It is preferred that the shield 18 cover the distal end 22 of the needle 16 with the shield 18 being fixed to the needle carrier 14 with engagement of the first locking arrangement 38. With retraction of the proximal end 24 of the needle 16 and the covering of the distal end 22 of the needle 16 by the shield 18, both ends of the needle 16 may be covered post-injection.

A second locking arrangement 52 may be provided for fixing the needle carrier 14 to the hub 12, particularly with the proximal end 24 of the needle 16 being in the retracted state. The second locking arrangement 52 may be of any configuration which is engageable with sufficient relative movement, e.g., axial movement, between the needle carrier 14 and the hub 12. By way of non-limiting example, the needle carrier 14 may be provided with a secondary detent 54 for snap engagement with a secondary recess 56 formed in the hub 12. The needle carrier 14 is formed with sufficient inherent memory to maintain snap engagement between the secondary detent 54 and the secondary recess 56. It is preferred that the secondary detent 56 be provided on a secondary cantilevered arm 58. Alternatively, the constituent material of the needle carrier 14 may be utilized to provide the inherent memory. As will be appreciated by those skilled in the art, a plurality of the second locking arrangements 52 may be provided (e.g., a plurality of sets of secondary detents 54/secondary recesses 56).

A secondary ramped surface 60 is preferably provided adjacent to the secondary recess 56 to allow the secondary detent 54 to by-pass in one direction, over the secondary ramped surface 60 in a rising direction. The secondary ramped surface 60 defines a secondary step 62 adjacent to the secondary recess 56 to inhibit movement of the secondary detent 54 in the reverse direction. A secondary channel 64 may be provided in the hub 12 formed to accommodate sliding movement of the secondary detent 54. Preferably, the secondary channel 64 is generally parallel to a longitudinal axis of the hub 12 and longitudinally aligned with the secondary recess 56.

During use, with sufficient distal movement of the needle carrier 14 relative to the hub 12, the second locking arrangement 52 may be engaged whereby the needle carrier 14 becomes fixed to the hub 12. This distal movement shall occur with the shield 18 fixed to the needle carrier 14. The second locking arrangement 52 is preferably engaged with the proximal end 24 of the needle 16 being in the retracted state.

The secondary detent 54 may be also used to releaseably fix the needle carrier 14 to the hub 12, for example, by being seated in an initial position in initial recess 66. The initial recess 66 is preferably longitudinally aligned with the secondary channel 64. In addition, it is preferred that angled surface 68 be located adjacent to the initial recess 66 configured to provide a rising surface in a distal direction to facilitate removal of the secondary detent 54 from the initial recess 66 upon a threshold amount of force being applied to urge the secondary detent 54 in a distal direction relative to the hub 12. It is preferred that the angled surface 68 be provided with a greater angle of inclination than the secondary ramped surface 60 so that the angled surface 68 provides resistance against movement thereacross by the secondary detent 54, such resistance being surmountable. The secondary detent 54 may act to maintain the needle carrier 14 in a fixed position relative to the hub 12 with the shield 18 being initially distally displaced prior to the first locking arrangement 38 being engaged.

It is preferred to maintain radial alignment of the needle carrier 14 with the hub 12, particularly with the secondary detent 54 being seated in the secondary channel 64. Torque may be applied to the safety pen needle assembly 10 during mounting onto the injector I (for example, with the feature 20 being threads). To limit possible relative rotation between the needle carrier 14 and the hub 12 as a result of the applied torque, an alignment groove 70 may be formed in the hub 12 with a corresponding alignment tooth 72 being formed on the needle carrier 14. As shown in FIG. 17, the alignment tooth 72 is seated in the alignment groove 70 so as to inhibit rotational movement between the needle carrier 14 and the hub 12, yet permit relative longitudinal movement therebetween. A plurality of sets of alignment grooves 70/alignment teeth 72 may be provided.

In an initial state, as described above, the shield 18 is moveable relative to the needle carrier 14. The shield 18 may be releasably fixed to the needle carrier 14 to define an initial position. For example, primary recess 74 may be provided in the needle carrier 14, located proximally of the recess 42 along the channel 50. The detent 40 may be seated in the primary recess 74 in an initial state of the safety pen needle assembly 10, prior to use. As will be appreciated by those skilled in the art, the relative positioning of the primary recess 74 will define whether the distal end 22 of the needle 16 will be covered in an initial state. Thus, with reference to FIG. 2, it is preferred that the primary recess 74 be located so that the shield 18 in fact covers the distal end 22 in an initial state.

Figure 8:
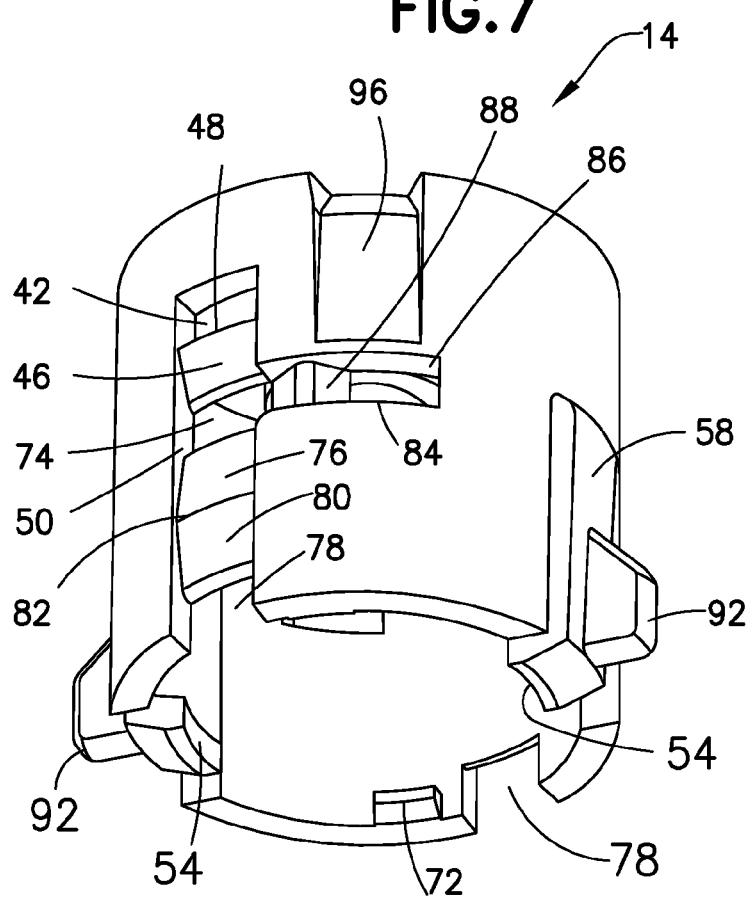
Figure 9:
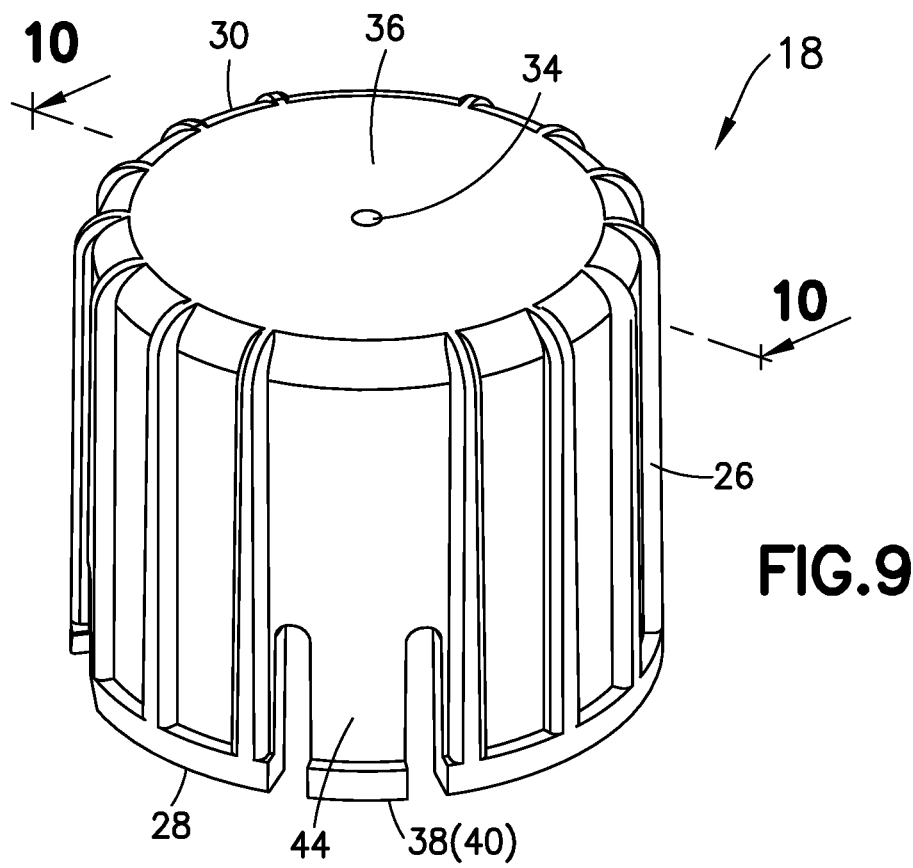
FIGS. 9-11 are various views of a shield useable with the subject invention; and, FIGS. 12-17 show a safety pen needle assembly formed in accordance with the subject invention in use.
Figure 10:
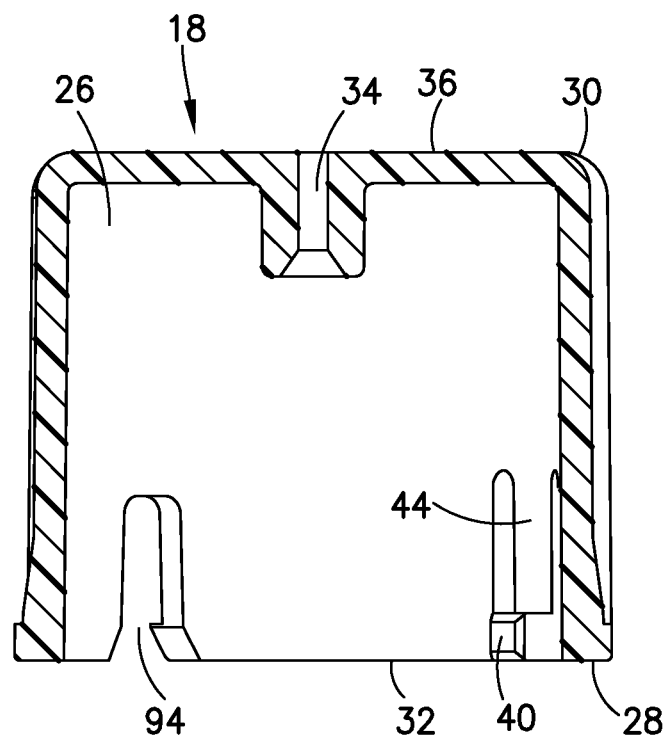
Figure 11:
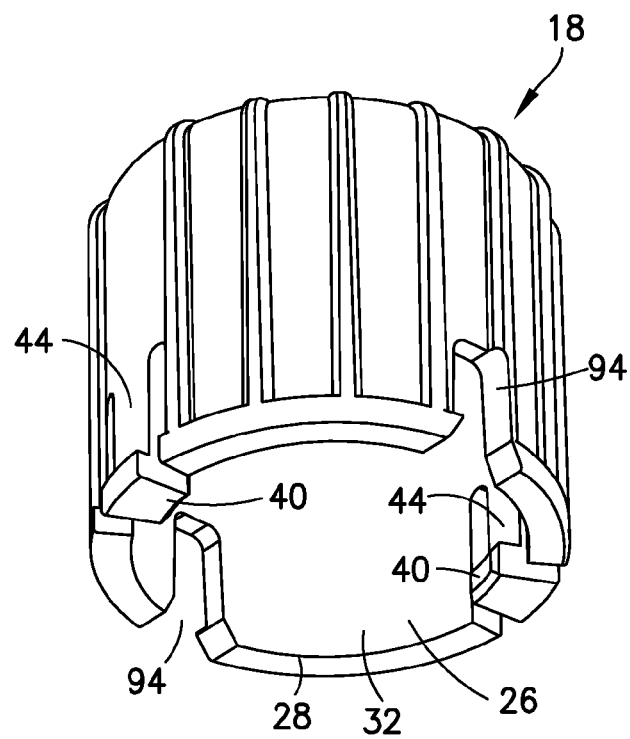
Figure 12:
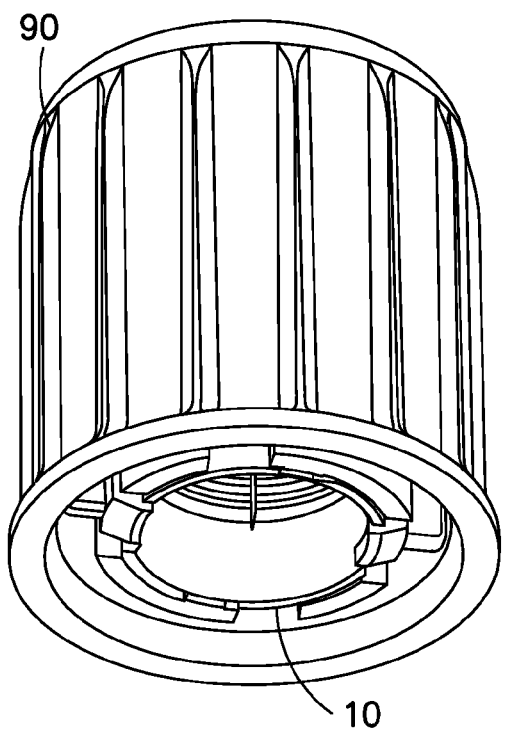

It is preferred that the channel 50 be provided with sufficient length in a proximal direction so as to permit movement of the detent 40 proximally, with the shield 18 being retracted during use, particularly to expose the needle 16 sufficiently to perform an injection. The primary recess 74 may be positioned between the ramped surface 46 and a primary ramped surface 76 configured to rise in a proximal direction away from the primary recess 74. Further, a holding recess 78 may be provided along the channel 50 formed to accommodate the detent 40, particularly with the shield 18 being in a position desired for injection. This allows for the shield 18 to be releasably fixed to the needle carrier 14 with a proper working length of the needle 16 being exposed for the injection. A holding ramped surface 80 may be provided adjacent to the holding recess 78. As best shown in FIG. 8, the primary ramped surface 76 and the holding ramped surface 80 may be disposed adjacent to one another so that both rise to a common ridge 82. With this arrangement, during use, the detent 40 of the shield 18 is initially seated in the initial recess 66 then advanced proximally to the holding recess 78 for the injection and then advanced distally into locking snap engagement with the recess 42 post-injection.

Figure 14:
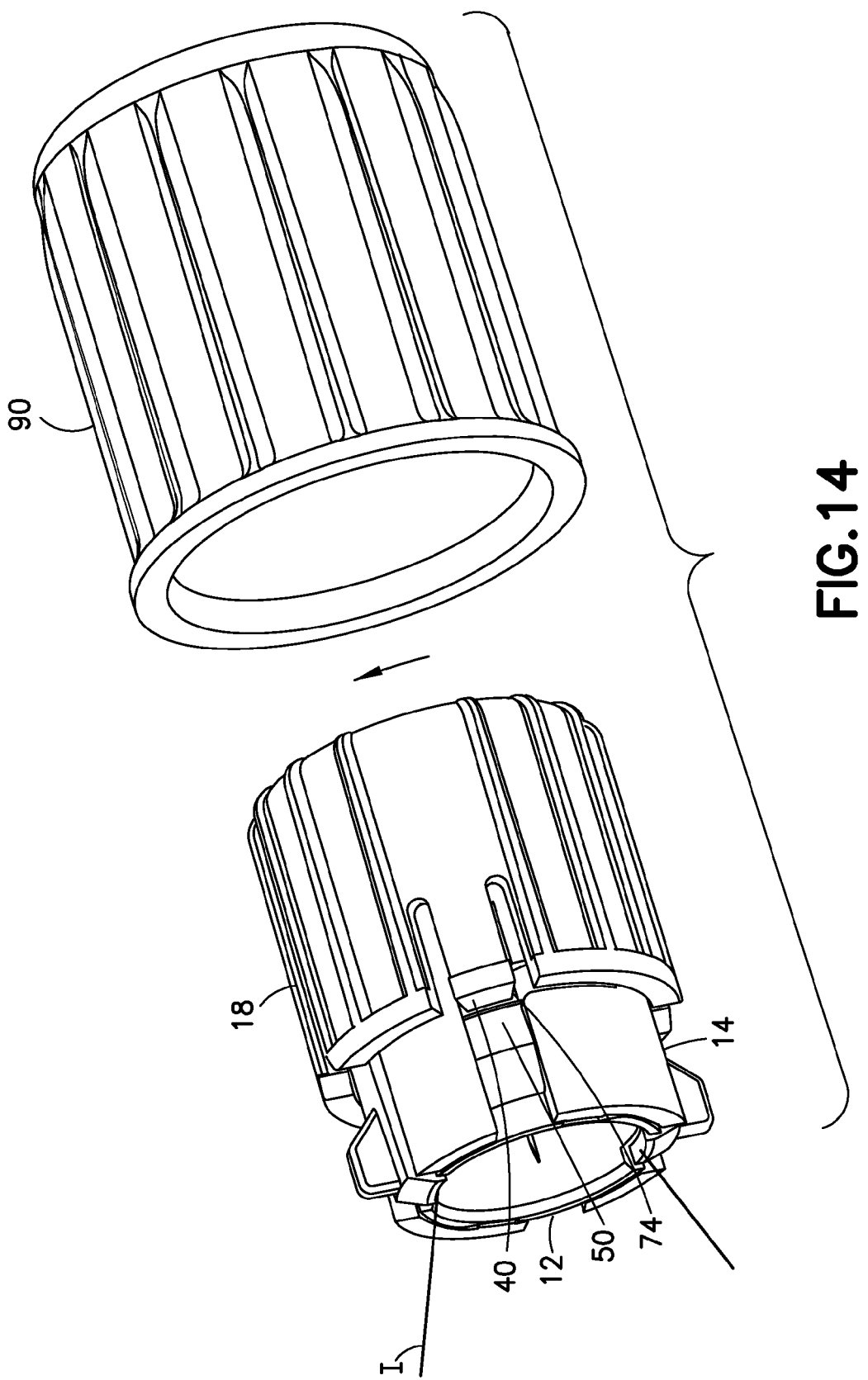

To limit inadvertent activation of the shielding prior to injection, a storage channel 84 may be defined in the needle carrier 14 disposed transversely to the channel 50. A storage recess 86 may be provided along the storage channel 84 having adjacent thereto a storage ramped surface 88. Prior to use, the detent 40 may be seated in the storage recess 86, out of longitudinal alignment with the channel 50. To prepare for use, with the hub 12 mounted onto the injector I, as shown in FIG. 14, the shield 18 may be rotated relative to the hub 12 to align the detent 40 in the channel 50; such alignment may result in the detent 40 being seated in the primary recess 74. It is noted that the feature 20 may be threads which require rotating mounting of the safety pen needle assembly 10 onto the injector I. It is thus preferred that the storage channel 84 extend from the channel 50 in a direction coincident with the direction of rotation necessary to mount the safety pen needle assembly 10 onto the injector I. Thus, for example, if clockwise rotation is required of the hub 12 relative to the injector I, it is preferred that the storage channel 84 extend generally in a clockwise direction away from the channel 50 (with viewing rotation from the same point). In this manner, the detent 40 is maintained in the storage recess 86 during mounting. In addition, torque applied to the shield 18 for mounting the safety pen needle assembly 10 may be transmitted through the interengagement of the detent 40 and the needle carrier 14, e.g., transmitted to the end of the storage channel 84.

In addition, the safety pen needle assembly 10 may be initially packed into a casing 90 for storage and transportation, as shown in FIGS. 1 and 2. A peelable foil or other covering may be applied to the casing 90 to seal the safety pen needle assembly 10 therein. To prevent inadvertently causing relative longitudinal movement between the needle carrier 14 and the hub 12 upon removal of the safety pen needle assembly 10 from the casing 90, one or more fins 92 may be provided on the secondary cantilevered arms 58. The fins 92 are dimensioned so as to restrict outward radial movement of the secondary detent 54 while in the casing 90. In this manner, the secondary detent 54 is caused to remain seated in the initial recess 66. Cut-outs 94 may be provided in the needle shield 18 as needed to slide over the fins 92 during use, for example, as shown in FIG. 15.

As shown in FIG. 17, the safety pen needle assembly 10 may be inserted into the casing 90 after use, at least partially, for disposal.

It is preferred that all of the components described herein, with the exception of the needle 16, be formed of a thermoplastic material. Each of the hub 12, the needle carrier 14, the shield 18 and the casing 90 may be separately and unitarily formed by molding, for example, injection molding. To facilitate assembly, one or more ramped assembly surfaces 96 may be provided on the needle carrier 14 to facilitate mounting of the shield 18 thereonto, particularly with the gradual passage of the detent 40 into the storage channel 84 with mounting the shield 18 during assembly onto the needle carrier 14. Likewise, the ramped assembly surfaces 96 may be provided on the hub 12 to permit gradual passage of the alignment tooth 72 into the alignment groove 70 with mounting the needle carrier 14 during assembly onto the hub 12.

What is claimed is:

1. A safety pen needle assembly comprising:
   a hub having features for mounting onto a medical injector;
   a needle carrier;
   a needle fixed to said needle carrier, said needle including proximal and distal ends, said distal end formed for insertion into a patient;
   a shield; and,
   first engageable locking means for fixing said shield to said needle carrier so that said shield and said needle carrier move in concert,
   wherein, in an initial state, said shield is moveable relative to said needle carrier,
   wherein, upon a predetermined extent of distal movement of said shield relative to said needle carrier, said first locking means is engaged such that said shield becomes fixed to said needle carrier, and
   wherein, upon further distal movement of said shield relative to said needle carrier beyond said predetermined extent of distal movement, said shield and said needle carrier move in concert together relative to said hub causing said proximal end of said needle to move distally relative to said hub to a retracted state.

2. A safety pen needle assembly as in claim 1, wherein said shield covers said distal end of said needle with said shield fixed to said needle carrier.

3. A safety pen needle assembly as in claim 1, further comprising second engageable locking means for fixing said needle carrier to said hub, said second locking means being engaged upon a secondary predetermined extent of distal movement of said needle carrier relative to said hub.

4. A safety pen needle assembly as in claim 3, wherein with said second locking means being engaged such that said needle carrier is fixed to said hub, said proximal end of said needle is in said retracted state.

5. A safety pen needle assembly as in claim 3, wherein said shield is fixed to said needle carrier with said needle carrier moving said secondary predetermined extent of distal movement relative to said hub.

* * * * *